US00PP14046P29

(12) United States Plant Patent
Kientzler

(10) Patent No.: US PP14,046 P2
(45) Date of Patent: Aug. 5, 2003

(54) NEW GUINEA IMPATIENS PLANT NAMED 'KIPAQUI'

(75) Inventor: Ludwig Kientzler, Gensingen (DE)

(73) Assignee: Innovaplant GmbH & Co. KG, Gensingen (DE)

( * ) Notice: Subject to any disclaimer, the term of this patent is extended or adjusted under 35 U.S.C. 154(b) by 0 days.

(21) Appl. No.: 10/159,069

(22) Filed: May 31, 2002

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Kipaqui', characterized by its rounded, upright and compact plant habit; freely branching growth habit; dark green-colored foliage; freely flowering habit with flowers positioned above or beyond the foliage; and red purple-colored flowers with darker red purple-colored centers.

1 Drawing Sheet

BOTANICAL CLASSIFICATION/CULTIVAR DESIGNATION

*Impatiens hawkeri* cultivar Kipaqui.

BACKGROUND OF THE INVENTION

The present Invention relates to a new and distinct cultivar of New Guinea Impatiens plant, botanically known as *Impatiens hawkeri*, and hereinafter referred to by the cultivar name Kipaqui.

The new Impatiens is a product of a planned breeding program Inventor in Gensingen, Germany. The objective of the breeding program is to develop new Impatiens cultivars with interesting and unique flower and foliage colors.

The new Impatiens originated from a cross-pollination made by the Inventor in September, 1997 of the *Impatiens hawkeri* cultivar Kinic, disclosed in U.S. Plant Pat. No. 11,412, as the female, or seed parent, with a proprietary *Impatiens hawkeri* selection identified as LL 739, not patented, as the male, or pollen parent. The cultivar Kipaqui was discovered and selected by the Inventor as a flowering plant within the progeny of the stated cross-pollination in a controlled environment in Gensingen, Germany in April, 1998.

Asexual reproduction of the new cultivar by terminal cuttings taken at Gensingen, Germany, since May, 1998, has shown that the unique features of this new Impatiens are stable and reproduced true to type in successive generations.

SUMMARY OF THE INVENTION

The following traits have been repeatedly observed and are determined to be the unique characteristics of 'Kipaqui'. These characteristics in combination distinguish 'Kipaqui' as a new and distinct Impatiens cultivar:

1. Rounded, upright and compact plant habit.

2. Freely branching growth habit; bushy appearance.

3. Dark green-colored foliage.

4. Freely flowering habit with flowers positioned above or beyond the foliage.

5. Red purple-colored flowers with darker red purple-colored centers.

Plants of the new Impatiens differ from plants of the female parent, the cultivar Kinic, in the following characteristics:

1. Plants of the new Impatiens are larger and more mounded than plants of the cultivar Kinic.

2. Plants of the new Impatiens have larger leaves than plants of the cultivar Kinic.

3. Plants of the new Impatiens have larger flatter flowers than plants of the cultivar Kinic.

4. Plants of the new Impatiens have red purple-colored flowers whereas plants of the cultivar Kinic have pink-colored flowers.

Plants of the new Impatiens differ from plants of the male parent, the selection LL 739, in the following characteristics:

1. Plants of the new Impatiens are not as vigorous as plants of the selection LL 739.

2. Plants of the new Impatiens have more green-colored leaves than plants of the selection LL 739.

3. Plants of the new Impatiens flower earlier than plants of the selection LL 739.

4. Plants of the new Impatiens have red purple-colored flowers whereas plants of the selection LL 739 have dark purple-colored flowers.

Plants of the new Impatiens can be compared to plants of the cultivar Kicarl, disclosed in U.S. Plant Pat. No. 11,370. In side-by-side comparisons conducted in Gensingen, Germany, plants of the new Impatiens differed from plants of the cultivar Kicarl in the following characteristics:

1. Plants of the new Impatiens were more compact and not as vigorous as plants of the cultivar Kicarl.

2. Plants of the new Impatiens had more green-colored leaves than plants of the cultivar Kicarl.

3. Plants of the new Impatiens had smaller flowers than plants of the cultivar Kicarl.

4. Plants of the new Impatiens were more freely flowering than plants of the cultivar Kicarl.

5. Plants of the new Impatiens had lighter colored flowers than plants of the cultivar Kicarl.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Impatiens. The photograph comprises a side perspective view of a typical flowering plant of 'Kipaqui' grown in a 15-cm container.

DETAILED BOTANICAL DESCRIPTION

The cultivar Kipaqui has not been observed under all possible environmental conditions. The phenotype may vary somewhat with variations in environment such as temperature and light intensity, without, however, any variance in genotype. The aforementioned photograph and the following observations and measurements describe plants grown in Encinitas, Calif., during the late spring, under commercial practice in a polyethylene-covered greenhouse with day temperatures about 24° C., night temperatures about 18° C., and light levels typically about 4,000 foot-candles. Plants used in the photograph and following description were about 14 weeks old and grown in 15-cm containers with one plant per container.

In the following description, color references are made to The Royal Horticultural Society Colour Chart, 1995 Edition, except where general terms of ordinary dictionary significance are used.

Botanical classification: *Impatiens hawkeri* cultivar Kipaqui.

Parentage:

*Female, or seed, parent.*—*Impatiens hawkeri* cultivar Kinic, disclosed in U.S. Plant Pat. No. 11,412.

*Male, or pollen, parent.*—Proprietary *Impatiens hawkeri* selection identified as LL 739, not patented.

Propagation:

*Type cutting.*—Terminal cuttings.

*Time to initiate roots.*—Summer: About 14 days at 21° C. Winter: About 18 days at 21° C.

*Time to produce a rooted cutting or liner.*—Summer: About 21 days at 21° C. Winter: About 24 days at 21° C.

*Root description.*—Fine, fibrous, and freely branching.

Plant description:

*General appearance.*—Rounded and somewhat upright; compact. Appropriate for 10 to 25-cm containers; multiple plants are typically planted in larger compainers.

*Growth and branching habit.*—Freely branching with about six lateral branches developing at the base, dense and bushy growth. Pinching, that is, removal of the terminal apices, is typically not required. Moderately vigorous.

*Plant height.*—About 10 cm.

*Plant diameter.*—About 17 cm.

*Lateral branches.*—Length: About 9 cm. Diameter: About 4 mm. Internode length: About 1.6 cm. Texture: Smooth, glabrous. Color: 59A.

*Foliage description.*—Arrangement: Opposite or in whorls; simple. Length: About 5.6 cm. Width: About 3 cm. Shape: Elliptic. Apex: Acuminate. Base: Attenuate. Margin: Serrulate with ciliation. Texture, upper and lower surfaces: Smooth, glabrous. Color: Young and fully expanded foliage, upper surface: 147A. Young and fully expanded foliage, lower surface: 147B. Venation, upper surface: 60B. Venation, lower surface: 59A. Petiole: Length: About 2 cm. Diameter: About 3 mm. Texture, upper and lower surfaces: Smooth, glabrous. Color, upper and lower surfaces: 59A.

Flower description:

*Flower type and flowering habit.*—Single axillary flowers. Freely flowering, usually about seven flowers and flower buds per lateral branch. Flowers positioned above and beyond the foliage and typically face upward or outward. Flowers somewhat cupped and rounded rectangular in shape. Flowers last about eight days on the plant depending on temperature and weather conditions. Petals self-cleaning; gynoecium persistent. Flowers not fragrant.

*Flowering season.*—Year-round under greenhouse conditions. In the garden, flowering from spring until fall.

*Flower height.*—About 4.6 cm.

*Flower width.*—About 4.2 cm.

*Flower depth.*—About 2.2 cm.

*Flower buds* (*at stage of showing color*).—Rate of opening: From showing color to fully open flower, typically about 2 to 3 days depending on temperature. Length: About 1.3 cm. Diameter: About 7 mm. Shape: Ovoid. Color: 63A.

*Petals.*—Quantity: Single, five per flower. Length: Banner petal: About 2.1 cm. Lateral petals: About 2.3 cm. Base petals: About 2.8 cm. Width: Banner petal: About 3.3 cm. Lateral petals: About 2.2 cm. Base petals: About 2.5 cm. Shape: Cordate. Apex: Emarginate. Base: Acute. Margin: Entire. Texture: Smooth; velvety. Color: When opening, upper surface: 57A. When opening, lower surface: 57C. Fully opened, upper surface: Towards margin and center, 57B; towards lateral edges, 57D; towards base, 58A; color fading to 68B to 68C with subsequent development. Fully opened, lower surface: 57D.

*Spur.*—Length: About 5 cm. Texture: Smooth, glabrous. Color: 59A to 59B.

*Peduncles.*—Length: About 3.5 cm. Diameter: About 1 mm. Strength: Strong. Angle: About 35° from vertical. Texture: Smooth, glabrous. Color: 59A.

*Reproductive organs.*—Androecium: Stamen number: Five fused at anthers, filaments free. Anther shape: Obovate. Anther size: About 3 mm by 3 mm. Anther color: 8C. Amount of pollen: Scarce to moderate. Pollen color: 8C. Gynoecium: Pistil length: About 4 mm. Stigma color: 155A. Style color: 155A. Ovary color: 144A.

*Seed/fruit.*—Seed and fruit development has not been observed.

Disease/pest resistance: Plants of the new Impatiens have not been observed to be resistant to pathogens and pests common to Impatiens.

Temperature tolerance: Plants of the new Impatiens have been observed to tolerate temperatures from 14 to 30° C.

It is claimed:

1. A new and distinct cultivar of New Guinea Impatiens plant named 'Kipaqui', as illustrated and described.

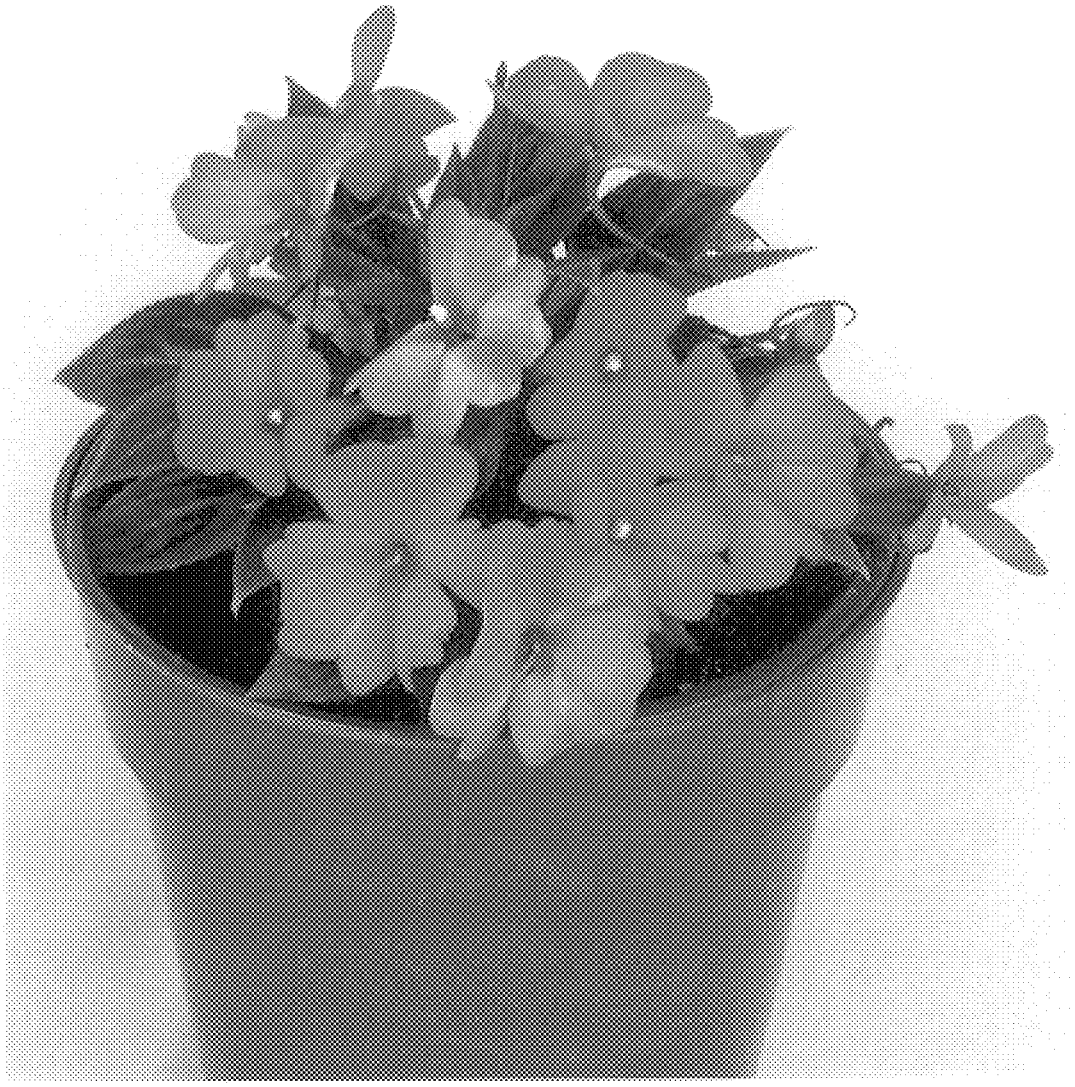

* * * * *